United States Patent [19]

Cremins et al.

[11] Patent Number: 4,978,624
[45] Date of Patent: Dec. 18, 1990

[54] REAGENT FOR THE DETERMINATION OF A DIFFERENTIAL WHITE BLOOD CELL COUNT

[75] Inventors: John F. Cremins, Waterbury, Conn.; Young R. Kim, Hartsdale, N.Y.; Michael J. Malin, Park Ridge, N.J.; Louis D. Sclafani, Carmel, N.Y.

[73] Assignee: Technicon Instruments Corporation, Tarrytown, N.Y.

[21] Appl. No.: 244,185

[22] Filed: Sep. 14, 1988

Related U.S. Application Data

[60] Division of Ser. No. 9,423, Feb. 2, 1987, Pat. No. 4,801,549, which is a continuation of Ser. No. 773,166, Sep. 6, 1985, abandoned.

[51] Int. Cl.$^5$ ..................... G01N 31/00; G01N 33/48
[52] U.S. Cl. ......................... 436/17; 436/10; 436/18; 436/63
[58] Field of Search ................. 436/10, 17, 18, 63

[56] References Cited

U.S. PATENT DOCUMENTS

| 3,741,875 | 6/1973 | Ansley et al. | 436/63 X |
|---|---|---|---|
| 3,884,579 | 5/1975 | Mauthner | 436/17 X |
| 4,040,785 | 8/1977 | Kim et al. | 436/18 X |
| 4,099,917 | 7/1978 | Kim | 436/10 |
| 4,185,964 | 1/1980 | Lancaster | 436/66 X |
| 4,286,963 | 9/1981 | Ledis et al. | 436/63 |
| 4,389,490 | 6/1983 | Crews et al. | 436/17 |
| 4,506,018 | 3/1985 | North | 436/10 |
| 4,528,274 | 7/1985 | Carter et al. | 436/10 |
| 4,529,705 | 7/1985 | Larsen | 436/10 X |
| 4,572,899 | 2/1986 | Walker et al. | 436/17 X |

Primary Examiner—Robert J. Hill, Jr.
Attorney, Agent, or Firm—Jeffrey M. Greenman

[57] ABSTRACT

This invention relates to a method for the rapid determination of a differential white blood cell count in a sample, which method comprises:
(a) preparing a reagent solution comprising formaldehyde or paraformaldehyde; a surfactant; a sugar or sugar alcohol; and a buffer; and
(b) rapidly mixing the reagent solution with the sample to be analyzed to form a reaction mixture, wherein both the reagent solution and the sample are initially at room temperature; and
(c) rapidly heating the reaction mixture to a temperature of from about 62° C. to about 72° C. in order to lyse the red blood cells in the sample and fix the white blood cells in said sample. The invention also relates to the reagent solution of part (a) of the method.

16 Claims, 8 Drawing Sheets

REAGENT FOR THE DETERMINATION OF A DIFFERENTIAL WHITE BLOOD CELL COUNT

This is a divisional of co-pending application Ser. No. 009,423, filed Feb. 2, 1987, now U.S. Pat. No. 4,801,549, which is a continuation of application Ser. No. 06/773,166, filed Sept. 6,1985, now abandoned.

BACKGROUND OF THE INVENTION

There are five classes of normal white blood cells or leukocytes: neutrophils, lymphocytes, monocytes, eosinophils and basophils. It is a known medical diagnostic procedure to examine a dried, stained smear of blood on a microscope slide to determine the relative proportions of these five normal types of white blood cells, as well as the concentration of any abnormal cells. Such procedure is referred to as a differential white blood cell count and is described in Miale, J. B., "Laboratory Medicine—Hematology", pp. 822–830, 1126, 1127 and 1130, C. V. Mosby Company, St. Louis, Missouri (1967).

Recently, automated processes and automated flow system apparatus therefor have been developed to ease the burden of differential white blood cell counting, such as described in U.S. Pat. No. 3,741,875 and 4,099,917. These use cytochemical procedures to specifically identify and label individual cell types.

The procedure for preparing a cell suspension for use in such systems comprises treating an uncoagulated blood sample with a surfactant for about 1.5 minutes to precondition the red blood cells for lysis; thereafter adding a fixative to the cells for about 1 minute while maintaining a neutral pH; and incubating the mixture at 58° C. to 60° C. for about 2 minutes to lyse the red blood cells and fix the white blood cells, as described in U.S. Pat. No. 4,099,917. It is imperative in such processes that all of the red blood cells be lysed because the red blood cells outnumber the white blood cells by about 700 to 1. Because of this, even if one percent of the red blood cells remain unlysed, the differential white blood cell count cannot be accurately arrived at.

A major drawback to the prior art methods is the relatively extended period of time each analysis requires, e.g., as much as five minutes just to prepare the cell suspension, thereby rendering such methods undesirable for emergency sample analysis or for other situations in which rapid results are desirable. Accordingly, there is need for a method for the determination of a differential white blood cell count which is relatively rapid as compared to the prior art procedures. Such a method would have to completely lyse the red blood cells in the sample without damaging the white blood cells, causing no extra-cellular precipitation or clumping of cells, since such precipitates or cell clumps could generate ambiguities in the cell detecting and recognizing phase of the process.

SUMMARY OF THE INVENTION

The present invention relates to a method for the rapid determination of a differential white blood cell count in a sample More particularly, the invention relates to a method which comprises:
 (a) preparing a reagent solution comprising
    formaldehyde or paraformaldehyde;
    a surfactant;
    a sugar or sugar alcohol; and
    a buffer; and
 (b) rapidly mixing said reagent solution with the sample to be analyzed to form a reaction mixture, wherein both said reagent solution and said sample are initially at a temperature of from about 20° C. to about 28° C.; and
 (c) heating said reaction mixture to a temperature of from about 62° C. to about 72° C. within about 30 seconds in order to lyse the red blood cells in said sample and fix the white blood cells in said sample.

BRIEF DESCRIPTION OF THE DRAWINGS

In the appended drawings, which are presented to further describe the invention and the assist in its understanding through clarification of its various aspects.

DETAILED DESCRIPTION OF THE INVENTION

The present invention relates to a method for the rapid determination of a differential white blood cell count and solution used therefor.

Formaldehyde or paraformaldehyde is used in the reagent solution of this invention as a fixative for the white blood cells. Preferably, formaldehyde is used and is present in said solution in an amount of from about 4.5% to about 6.6% weight volume (w/v). Ideally, formaldehyde is present in an amount of from about 5.3% to about 5.9% weight volume (w/v).

The surfactant present in the reagent solution of this invention is any one which will lyse the red blood cells (RBCs). For instance, the surfactant may be a neutral surfactant such as polyoxyethylene 20 sorbitan monolaurate, polyoxyethylene 23 monolauryl ether or polyoxyethylene 20 sorbitan monooleate, each of which may be readily synthesized by the skilled artisan, but is preferably the class of alkali metal salts of an alkyl sulfate having from about 10 to about 16 carbon atoms. The preferred alkali metal cations are sodium, potassium and lithium. The more preferred surfactants are the alkali metal dodecyl sulfates with sodium dodecyl sulfate being most preferred. The surfactant should be present in the reagent solution of this invention in an amount of about 0.36 mm. For sodium dodeoyl sulfate, this molar concentration corresponds to about 0.105 g/l.

The sugar or sugar alcohol is present in the reagent solution of this invention in order to raise the signal-to-noise ratio of the lymphocytes (i.e., to increase their ability to be "read" by electro optical detectors). Suitable sugars or sugar alcohols include sucrose, fructose, dextrose, sorbitol and mannitol. The choice between a sugar or a sugar alcohol should and can routinely be made by the skilled artisan based upon the particular requisites of the situation. Surprisingly, though, it has been found that when a sugar alcohol is used the reagent solution is more stable over time under stress conditions than when a reducing sugar such as glucose is used.

The reason for the increased stability of the reagent solution when a sugar alcohol is used rather than a reducing sugar appears to be that a reducing sugar such as glucose may, over time, be air oxidized to form gluconic acid, see, e.g., Nishikido, Jr., Tamura, W. and Fuknoka, Y., Jap. Kokai Tokyo Koho 80 40, 606, *Chem.*

Abs. 93:22120d (1950). If gluconic acid is present the pH of the solution is lowered. Once the pH falls outside of the range of this invention, the method of this invention becomes less accurate due to non-lysis of red cells. A sugar alcohol cannot be air-oxidized. In addition, a sugar alcohol may chemically combine with formaldehyde to form a polyacetal, thereby preventing the oxidation of formaldehyde to formic acid which, if formed, would lower the pH of the formulation.

The preferred sugar to be used in the reagent solution of this invention is dextrose (which is not a reducing sugar) and the preferred sugar alcohol is sorbitol, although as indicated, sugar alcohol is preferred. Dextrose or sorbitol should be present in an amount of from about 9.0% to about 13.5% weight/volume (w/v). Ideally, dextrose or sorbitol are present in the reagent solution of this invention in an amount of from about 11.0% to about 12.0% (w/v). When a sugar other than dextrose or a sugar alcohol other than sorbitol is used, the amount should be adjusted so that the alternate sugar or sugar alcohol is present on approximately an equimolar basis with dextrose or sorbitol.

If desired, a salt may also be included in the reagent solution. Salts suitable for use in the present invention may be alkali metal chloride salts such as NaCl, KCl and LiCl. Ideally, the salt is NaCl. Such salt is may optionally be present because it may aid in discriminating the neutrophils from the eosinophils by causing a difference in peroxidase stain intensity using light scatter/absorption optics. Other halogen salts (i.e., fluoride, bromide and iodide) over-inhibit peroxidase activity of the neutrophils, thereby preventing the discrimination of neutrophils from the other unstained white blood cells (WBCs). The salt, when used, should preferably be present in an amount of from about 68 mM to about 103 mM. When NaCl is used as the salt, it is present in said reagent solution in an amount of from about 0.4% to about 0.6% (w/v).

The buffer or mixture of buffers useful in this invention should be those suitable for maintaining the pH of the reagent solution at from about 6.6 to about 7.6, preferably from about 6.9 to about 7.3. Suitable buffers include sodium or potassuim phosphates, diethyl malonate, 3-(N-morpholino) propane sulfonic acid, (MOPS), N-2-acetamido-2-aminoethane sulfonic acid (ACES), and 4-(2-hydroxyethyl)-1-piperazine-ethanesulfonic acid (HEPES). Preferred is a mixture of $Na_2HPO_4$ and $NaH_2PO_4$. As indicated, the buffers should be present in the reagent solution of this invention in an amount suitable to maintain the pH of the solution at approximately neutral levels. For instance, when a mixture of $Na_2HPO_4$ and $NaH_2PO_4$ is used, the mixture should contain a mole ratio of $Na_2HPO_4$ to $NaH_2PO_4$ which is from about 2.04:1 to about 0.81:1 to produce a series of solutions with a pH range of about 6.9 to about 7.3. The concentration of such mixture in the reagent solution of this invention is from about 0.075 Molar (M) to about 0.125 M.

The reagent solution useful in the practice of this invention is an aqueous solution and, preferably, deionized water is used. The solution is prepared by combining the ingredients, in admixture, in water. A close watch should be maintained on the pH of the solution to ensure that it stays within the desired range. Additionally, the skilled artisan may also include other additives in the reagent solution as desired. For instance, ethylenediamine tetraacetic acid (EDTA) may be included as a metal chelator.

In practicing the method of this invention, the reagent solution is rapidly mixed with the sample to be analyzed to form the reaction mixture. Uniform mixture should occur within 5 seconds of the time the reagent solution and the blood sample come into contact with each other. If the two are not uniformly mixed rapidly, fixation of RBCs will occur which prevents complete lysis of the RBCs, thereby greatly impairing the accuracy of the differential WBC count obtained from the practice of this invention.

When mixed, the reagent solution and the blood sample should initially be at room temperature (about 20° C. to 28° C.) in order to ensure that the critical heating profile is maintained. The reaction mixture is then rapidly heated to a temperature of from about 62° C. to about 72° C., ideally from about 64° C. to about 68° C., preferably by injection into an automated hematology analyzer maintained at a suitably elevated temperature. Kinetic measurements indicate that the reaction mixture temperature is brought to from about 35° C. to about 42° C. substantially immediately upon injection. The subsequent temperature rise begins from that point. The heating of the reaction mixture should take place within about 30 seconds, preferably within about 20 seconds, otherwise RBC fixation will occur, preventing lysis, and thereby interfering with the accuracy of the differential WBC count.

Immediately thereafter, a staining mixture comprising hydrogen peroxide and a suitable chromogen such as 4-chloro-1-naphthol is mixed with the reaction mixture. The initial temperature of the staining mixture may be room temperature and, ideally but not necessarily, the temperature after mixing the staining mixture with the reaction mixture is increased to from about 62° C. to about 72° C., preferably from about 63° C. to about 69° C. in a period of within about 30 seconds preferably from about 8 to about 15 seconds, in order to stain the neutrophils and eosinophils which are peroxidase active.

In practice, the reaction may proceed as follows: an automated hematology analyzer reaction chamber is maintained at a temperature of approximately 72° C. 12.0 ul of whole blood and 250 ul of the reagent solution disclosed herein are simultaneously injected into the system at room temperature, thereby rapidly mixing the two to form the reaction mixture, which is then incubated for up to about 30 seconds, during which time the temperature of the mixture is increased to from about 62° C. to about 72° C. At the end of the incubation period, the RBCs are completely lysed and the WBCs fixed.

Immediately thereafter 125 ul of a chromogen mixture (for example, 0.8% weight/volume (w/v) 4-chloro-1-naphthol in oxydiethanol) is simultaneously injected with 250 ul of a hydrogen peroxide solution comprising 0.3% weight/volume (w/v) hydrogen peroxide. Both reagents are initially at room temperature, but due to the temperature of the reaction chamber, the staining mixture temperature is increased to from about 63° C. to about 69° C. within about 30 seconds, at which time the peroxidase staining of neutrophils and eosinophils is completed.

Figure 1:
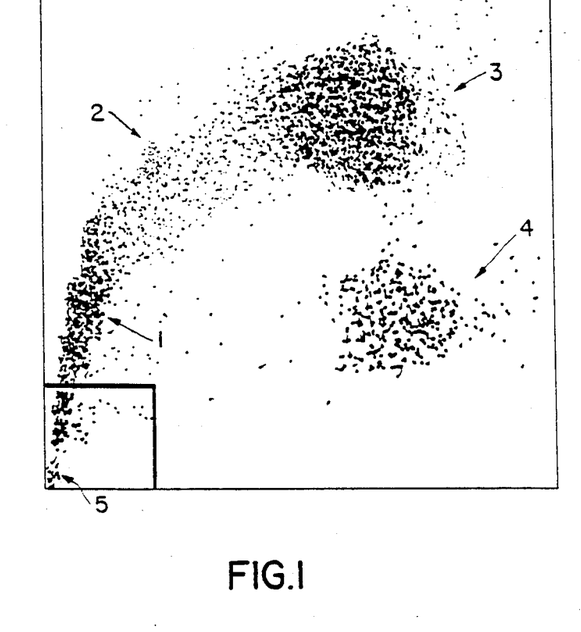
FIGS. 1 through 15 depict cytograms obtained when various reagent solutions prepared in accordance with the present invention were utilized in the determination of a differential white blood count by an automated hematology analyzer.

FIG. 1 illustrates a cytogram which is obtained from the electro-optical detection apparatus of an automated hematology analyzer. This figure shows the four WBC types differentiated by the method of this invention: 1, lymphocytes; 2, monocytes; 3, neutrophils, and 4, eosinophils. The cytogram also shows noise, 5, arising from platelets and red cell ghosts.

Another significant aspect of this invention is the high solute concentration of the reagent solution. The relatively high formaldehyde or paraformaldehyde and sugar or sugar alcohol contents combine to yield a total molarity of the reagent solution in excess of about 2.0 M/L. The effect of this hypertonic solution on blood cells causes them to crenate (shrink due to osmotically-driven dehydiation). It is known that crenation of the lymphocytes enchances their detection over noise thereby improving the accuracy of the differential WBC count determination.

Although the procedure of the subject invention is illustrated using automated equipment, it will be readily observed by those skilled in the art that it may also be applicable to manual methods. Further, the procedure of this invention has been illustrated using whole blood to arrive at the differential WBC count therein. It will be appreciated by those skilled in the art that the invention may also be employed with stock calibrator, control and other solutions of blood cells which are specifically prepared to calibrate and maintain apparatus accuracy. The use of the term "sample" herein is specifically intended to include either whole blood or other solutions which contain blood cells. The following examples are illustrative of the invention. Whereas they are presented to further facilitate an understanding of the inventive concepts, they are in no way to be interpreted as limiting the present invention.

EXAMPLE I

Solutions were prepared in accordance with the following formulation:

| sodium dodecyl sulfate | 0.105 g/L |
| NaCl | 5.0 g/L |
| formaldehyde | 55.0 g/L |
| dextrose | 112.0 g/L |
| Phosphate Buffer* | 0.079 M** |
| EDTA, disodium salt | 0.75 g/L |
| water | to volume |

*A mixture of NaH$_2$PO$_4$ and Na$_2$HPO$_4$.
**NaOH and/or HCl was added to bring each portion of the solution to the indicated pH.

Each of three solutions was prepared at a pH of 6.5, 7.2 and 7.5, respectively. 250 ul of each solution was then rapidly mixed (within 2 seconds) with 12 ul of whole blood and incubated for 20 seconds during which time the temperature was raised to approximately 70° C. 250 ul of a solution which contains 0.3% hydrogen peroxide and 125 ul of a solution which contains 0.8% 4-chloro-1-naphthol in oxydiethanol were then combined with the reaction mixtures and incubated for 20 seconds, during which time the temperature was raised to approximately 67°.

Figure 2:
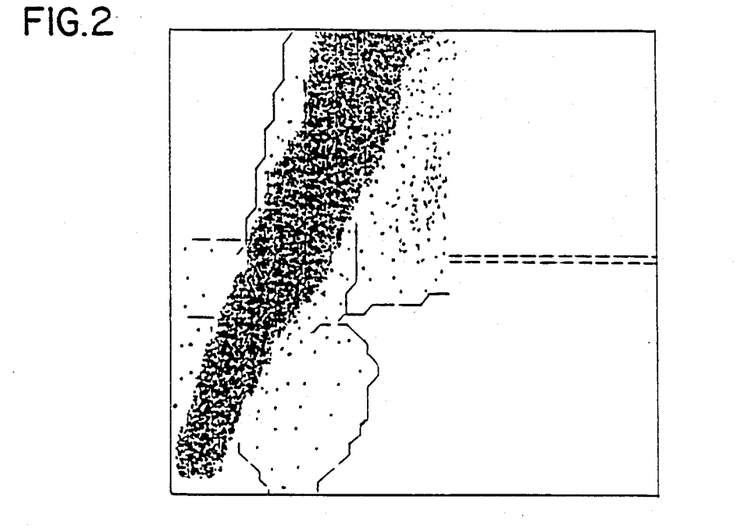

The resultant solutions were than passed through an electrooptical detection system and a cytogram prepared. FIG. 2 shows the cytogram obtained when the solution was at a pH of 6.5. This cytogram shows only the signature of red blood cells, illustrating that, at a pH of 6.5, RBCs are not lysed.

Figure 3:
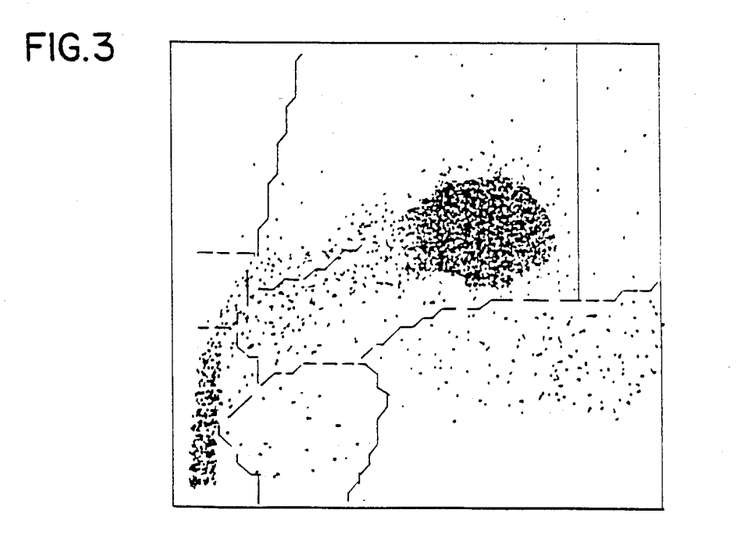

FIG. 3 shows the cytogram obtained when the solution was at a pH of 7.2. This cytogram shows a very distinct white cell distribution, illustrating that, at a pH of 7.2, RBCs are lysed and white cells appropriately fixed.

Figure 4:
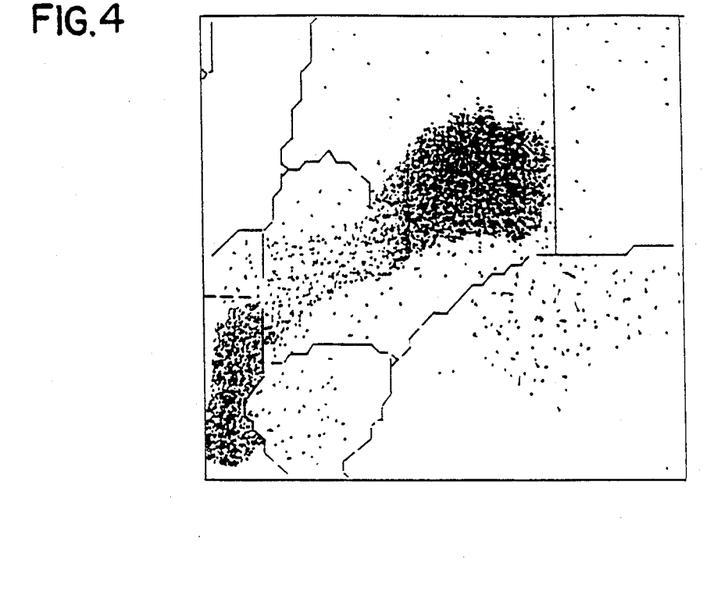
Figure 5:
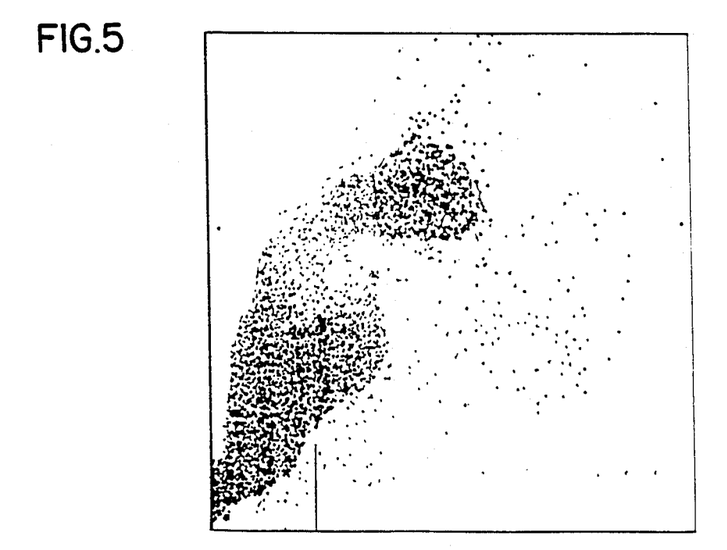
Figure 6:
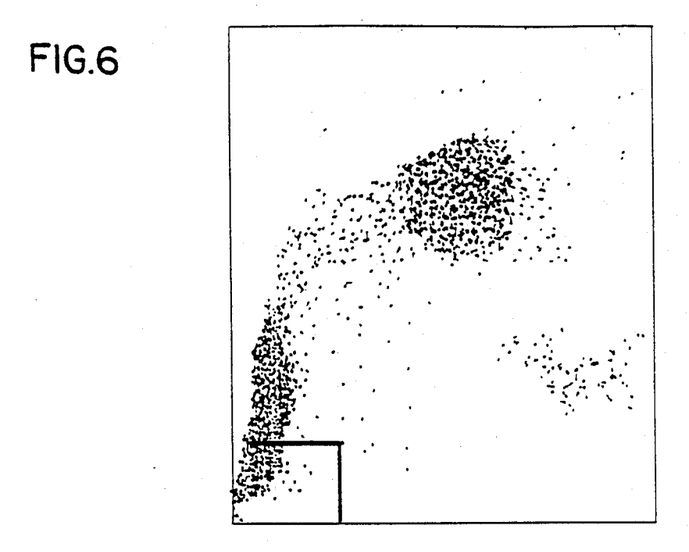
Figure 7:
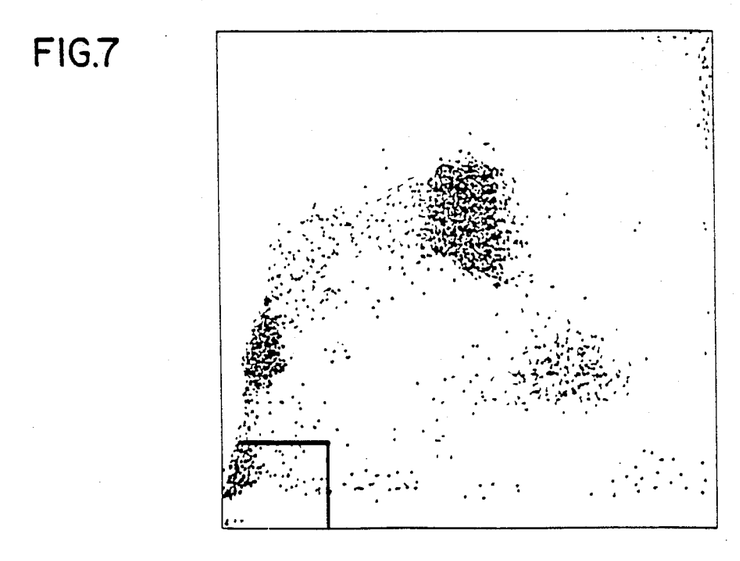
Figure 8:
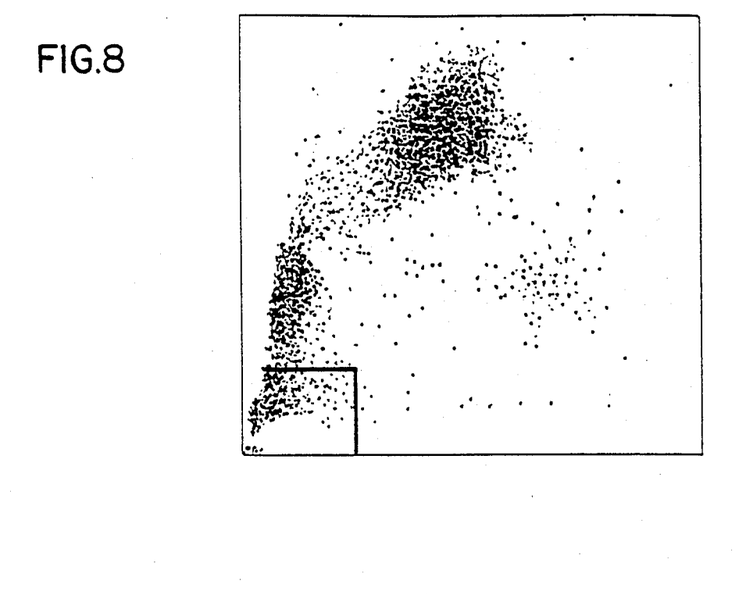
Figure 9:
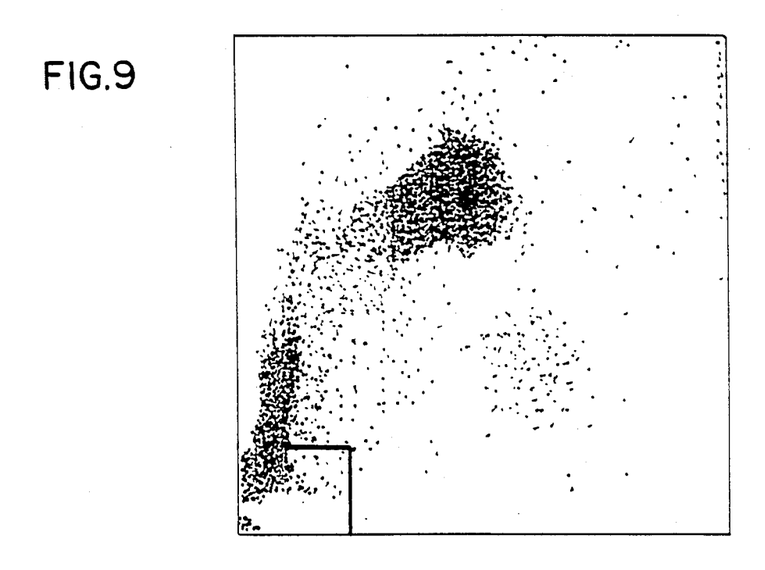
Figure 10:
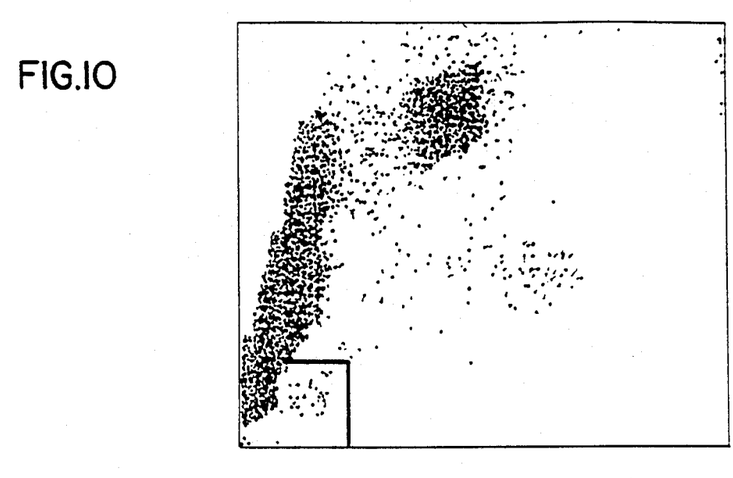

FIG. 4 shows the cytogram obtained when the solution was at a pH of 7.5. This cytogram shows a significant decrease in the lymphocyte and monocyte signatures illustrating that, at a pH of 7.5, RBCs are not completely lysed.

EXAMPLE III

Solutions were prepared in accordance with the following formulation:

| sodium dodecyl sulfate | 0.105 g/L |
| NaCl | 5.0 g/L |
| Phosphate Buffer* | 0.079 M |
| formaldehyde | 55.0 g/L |
| dextrose | ** |
| EDTA, disodium salt | 0.75 g/L |
| water | to volume |

*A mixture of NaH$_2$PO$_4$ and Na$_2$HPO$_4$ (pH approximately 7.0).
** Varied as described.

Four individual solutions were prepared, each having a different dextrose concentration. Each of these solutions was then reacted with whole blood as described in Example I.

Figure 11:
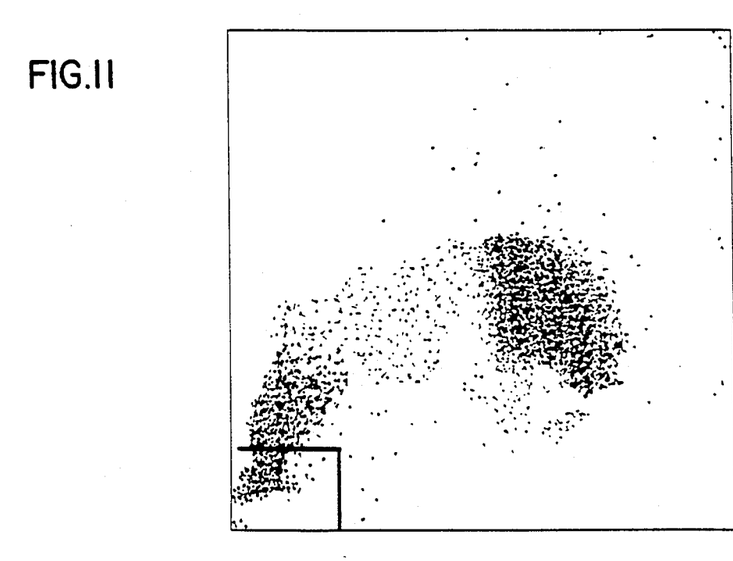

FIG. 11 shows the cytogram obtained when the dextrose concentration is 7.0%. This cytogram shows that the lymphocyte scatter signals are still too low to be clearly separated from the noise.

Figure 12:
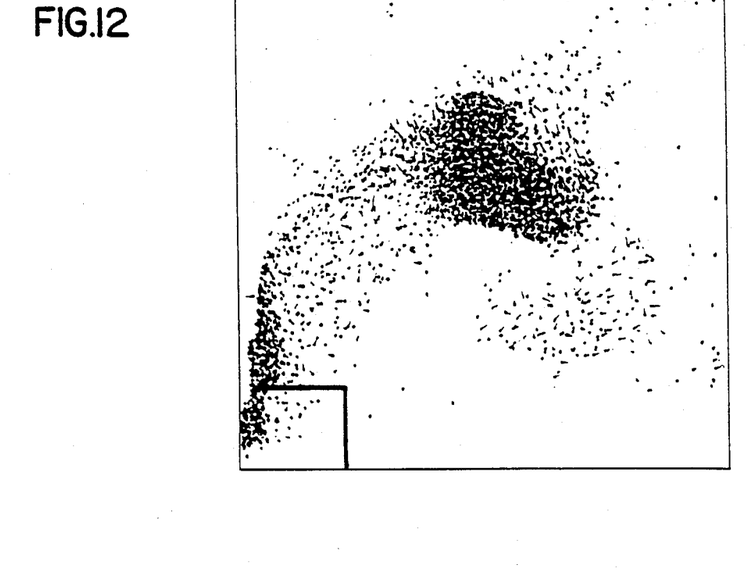

FIG. 12 shows the cytogram obtained when the dextrose concentration is 11.5%. This cytogram shows that the lymphocyte scatter signals are sufficiently high to be separated from the noise.

Figure 13:
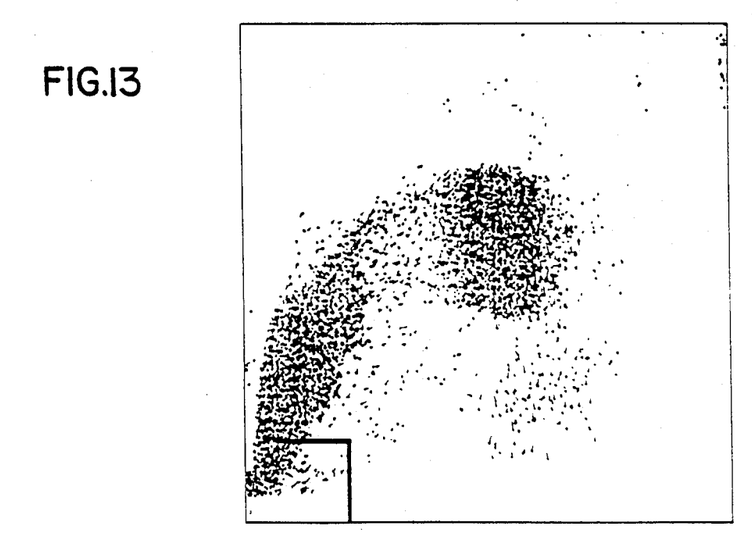

FIG. 13 shows the cytogram obtained when the dextrose concentration is 16.0%. This cytogram shows that precipitates have formed and that there is interference with complete RBC lysis.

EXAMPLE IV

Solutions were prepared in accordance with the following formulation:

| sodium dodecyl sulfate | 0.105 g/L |
| NaCl | 5.0 g/L |
| Phosphate Buffer* | 0.079 M** |
| formaldehyde | 55.0 g/L |
| sorbitol | 112.0 g/L |
| EDTA, disodium salt | 0.75 g/L |
| water | to volume |

*A mixture of NaH$_2$PO$_4$ and Na$_2$HPO$_4$.
**NaOH and/or HCl was added to bring each portion of the solution to the indicated pH.

The solution was divided into two portions, each of which was reacted with whole blood as described in Example I, except that the pH of each was varied.

Figure 14:
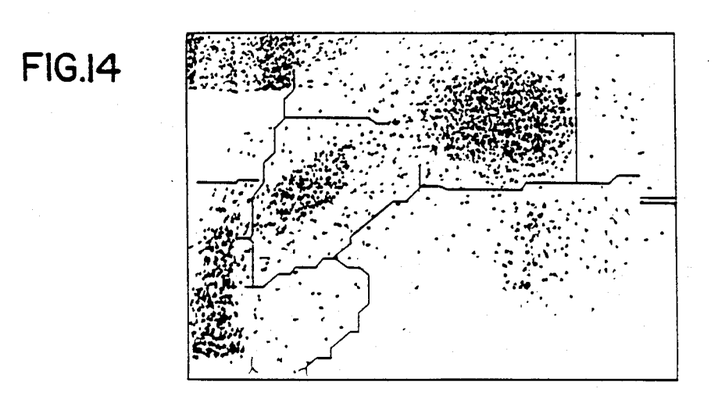
Figure 15:
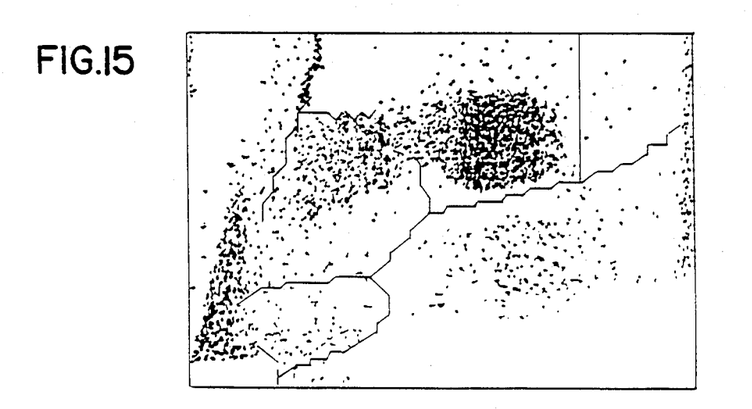

FIG. 14 shows the cytogram obtained when the solution was at a pH of 6.8. FIG. 15 shows the cytogram obtained when the solution was at a pH of 7.2. Each of these cytograms shows that a sugar alcohol may readily be substituted for a sugar in the reagent solution of this invention without loss of efficacy.

EXAMPLE V

The pH stability of components of the reagent solution of this invention was tested by inclusion of components in phosphate buffer (mixture of $Na_2HPO_4$ and $NaH_2PO_4$) over time at elevated temperatures. The results are shown in Table I.

TABLE I

| Solute | In 0.1 M phosphate buffer | | | | |
|---|---|---|---|---|---|
| | Days | Temp (°C.) | pH initial | pH final | ΔpH |
| Glucose[b] | 14 | 70 | 7.5 | 6.2 | −1.3 |
| Galactose[b] | 14 | 70 | 7.5 | 6.0 | −1.5 |
| Sorbitol[b] | 14 | 70 | 7.5 | 7.5 | 0 |
| Mannitol[b] | 14 | 70 | 7.5 | 7.5 | 0 |
| Formaldehyde[c] | 14 | 70 | 7.4 | 6.7 | −0.7 |
| Glucose[b] & Formaldehyde[c] | 6 | 70 | 7.2 | 6.7 | −0.5 |
| Sorbitol[b] & Formaldehyde[c] | 6 | 70 | 7.2 | 7.1 | −0.1. |
| Mannitol[b] & Formaldehyde[c] | 6 | 70 | 7.2 | 7.1 | −0.1. |
| Control[d] | 8 | 70 | 7.4 | 7.4 | 0 |

[b] Concentration is 0.7M
[c] Concentration is 1.8M.
[d] Buffer only.

It can readily be seen that the components, concentration and process parameters disclosed and claimed as this invention are critical to the proper determination of a differential WBC count which may be accomplished far more rapidly than prior art methods. Also, it can be seen that sugar alcohol provides more pH stability than a reducing sugar under stress conditions.

What is claimed is:

1. A composition for use as a reagent solution in the determination of a differential white blood cell count which comprises, in admixture, an aqueous solution of:
   (a) a surfactant;
   (b) formaldehyde in a concentration of from about 4.5% to about 6.6% weight/volume;
   (c) a sugar alcohol; and
   (d) a buffer to maintain the pH of said composition at between about 6.6 and 7.6.

2. The composition of claim 1 wherein said surfactant comprises an alkali metal salt of an alkyl sulfate containing from about 10 to about 16 carbon atoms.

3. The composition of claim 2 wherein said surfactant comprises an alkali metal dodecyl sulfate.

4. The composition of claim 3 wherein said surfactant is sodium dodecyl sulfate.

5. The composition of claim 2 wherein said surfactant is present in an amount of about 0.36 mm.

6. The composition of claim 1 wherein formaldehyde is present in an amount of from about 5.3% to about 5.9% weight/volume.

7. The composition of claim 1 wherein said sugar alcohol is selected from the group consisting of sorbitol and mannitol.

8. The composition of claim 7 wherein said sugar alcohol is sorbitol.

9. The composition of claim 7 wherein said sugar alcohol is present in an amount of from about 9.0% to about 13.5% weight/volume.

10. The composition of claim 9 wherein said sugar alcohol is present in an amount of from about 11.0% to about 12.0% weight/volume.

11. The composition of claim 1 which further comprises an alkali metal chloride salt.

12. The composition of claim 11 wherein said alkali metal chloride salt is selected from the group consisting of NaCl, KCl and LiCl.

13. The composition of claim 12 wherein said salt is NaCl.

14. The composition of claim 12 wherein said salt is present in an amount of from about 68 mM to about 103 mM.

15. The composition of claim 1 wherein the pH of said composition is from about 6.9 to about 7.3.

16. The composition of claim 1 wherein said buffer comprises a mixture of $Na_2HPO_4$ and $NaH_2PO_4$.

* * * * *